(12) United States Patent
Dlugos

(10) Patent No.: US 8,182,411 B2
(45) Date of Patent: May 22, 2012

(54) GASTRIC BAND WITH MATING END PROFILES

(75) Inventor: Daniel F. Dlugos, Middletown, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1409 days.

(21) Appl. No.: 11/182,070

(22) Filed: Jul. 15, 2005

(65) Prior Publication Data

US 2007/0015954 A1    Jan. 18, 2007

(51) Int. Cl.
*A61F 2/00* (2006.01)
(52) U.S. Cl. .......................................... 600/37; 606/157
(58) Field of Classification Search .................. 600/37, 600/29–32; 128/897–898; 606/151–158, 606/201–203
See application file for complete search history.

(56) References Cited

U.S. PATENT DOCUMENTS

| | | | |
|---|---|---|---|
| 4,592,339 A | 6/1986 | Kuzmak et al. |
| 4,696,288 A | 9/1987 | Kuzmak et al. |
| 4,760,837 A | 8/1988 | Petit |
| 5,033,481 A | 7/1991 | Heyler, III |
| 5,065,772 A | 11/1991 | Cox, Jr. |
| 5,074,868 A | 12/1991 | Kuzmak et al. |
| 5,083,576 A | 1/1992 | Ruiz-Razura et al. |
| 5,160,338 A | 11/1992 | Vincent |
| 5,226,429 A | 7/1993 | Kuzmak |
| 5,601,604 A | 2/1997 | Vincent |
| 5,658,298 A | 8/1997 | Vincent et al. |
| RE36,176 E | 3/1999 | Kuzmak |
| 5,910,149 A | 6/1999 | Kuzmak |
| 6,067,991 A | 5/2000 | Forsell |
| 6,102,922 A | 8/2000 | Jakobsson et al. |
| 6,210,347 B1 | 4/2001 | Forsell |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,511,490 B2 | 1/2003 | Robert |
| 6,547,801 B1 | 4/2003 | Dargent |

(Continued)

FOREIGN PATENT DOCUMENTS

EP    1319371    6/2003

(Continued)

*Primary Examiner* — John Lacyk

(57) ABSTRACT

A gastric band includes a belt and a balloon secured to the belt. The balloon and belt are shaped and dimensioned to circumscribe the stomach at a predetermined location. The balloon includes a longitudinally extending body having a first end and a second end, the first end and the second end respectively including mating profiles which align to create generally continuous surfaces along an outer surface of the gastric band and an inner surface of the gastric band as the outer surface and the inner surface transition between the first and second ends of the balloon.

9 Claims, 2 Drawing Sheets

U.S. PATENT DOCUMENTS

| | | |
|---|---|---|
| 6,676,674 B1 | 1/2004 | Dudai |
| 6,709,385 B2 | 3/2004 | Forsell |
| 6,915,165 B2 | 7/2005 | Forsell |
| 6,916,326 B2 | 7/2005 | Benchetrit |
| 6,953,429 B2 | 10/2005 | Forsell |
| 6,966,875 B1 | 11/2005 | Longobardi |
| 7,011,624 B2 | 3/2006 | Forsell |
| 2002/0198548 A1* | 12/2002 | Robert .......................... 606/157 |
| 2003/0019498 A1 | 1/2003 | Forsell |
| 2003/0032857 A1 | 2/2003 | Forsell |
| 2003/0066536 A1 | 4/2003 | Forsell |
| 2003/0092962 A1 | 5/2003 | Forsell |
| 2003/0105385 A1 | 6/2003 | Forsell |
| 2003/0114729 A1 | 6/2003 | Forsell |
| 2003/0158564 A1* | 8/2003 | Benchetrit ................... 606/151 |
| 2004/0049209 A1 | 3/2004 | Benchetrit |
| 2004/0153106 A1* | 8/2004 | Dudai .......................... 606/157 |
| 2004/0158272 A1 | 8/2004 | Hofle et al. |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2005/0002984 A1 | 1/2005 | Byrum et al. |
| 2005/0038458 A1 | 2/2005 | Bailly et al. |
| 2005/0070937 A1* | 3/2005 | Jambor et al. ................ 606/153 |
| 2005/0119672 A1 | 6/2005 | Benchetrit |
| 2005/0183730 A1 | 8/2005 | Byrum et al. |
| 2005/0187566 A1 | 8/2005 | Byrum et al. |
| 2005/0277963 A1 | 12/2005 | Fields |
| 2006/0074439 A1 | 4/2006 | Garner et al. |
| 2006/0229696 A1* | 10/2006 | Boustani et al. ............. 623/1.11 |

FOREIGN PATENT DOCUMENTS

| | | |
|---|---|---|
| EP | 1342458 A1 | 9/2003 |
| WO | WO 98/56231 A1 | 12/1998 |
| WO | WO2004/108025 | 12/2004 |
| WO | WO2005/072195 | 8/2005 |
| WO | WO2005/072664 | 8/2005 |

* cited by examiner

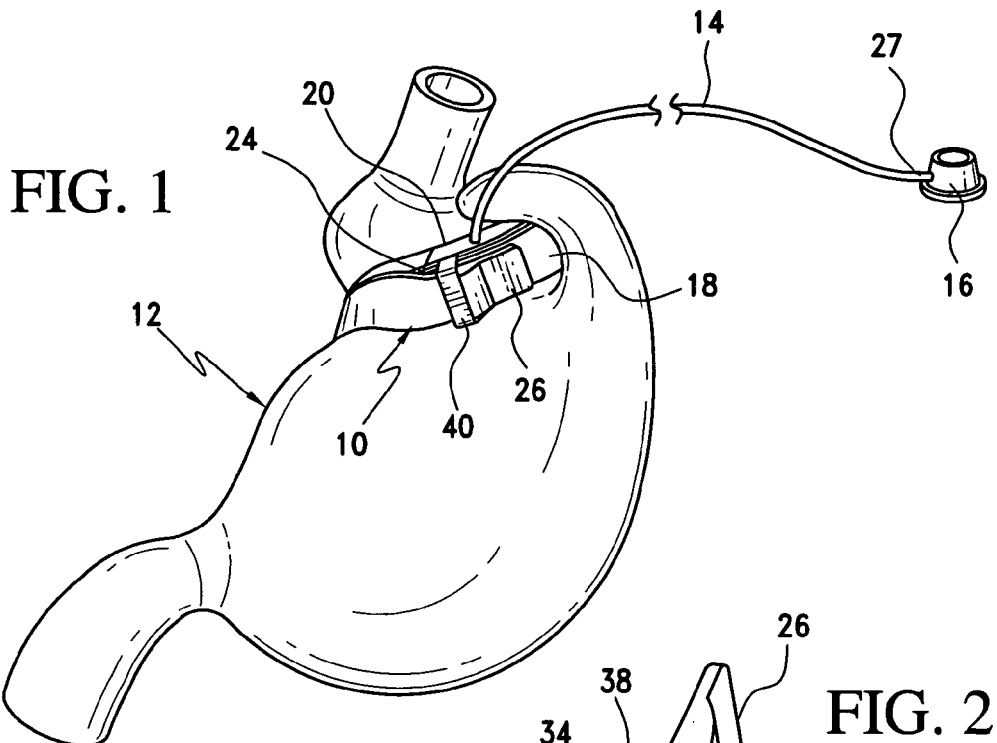
FIG. 1
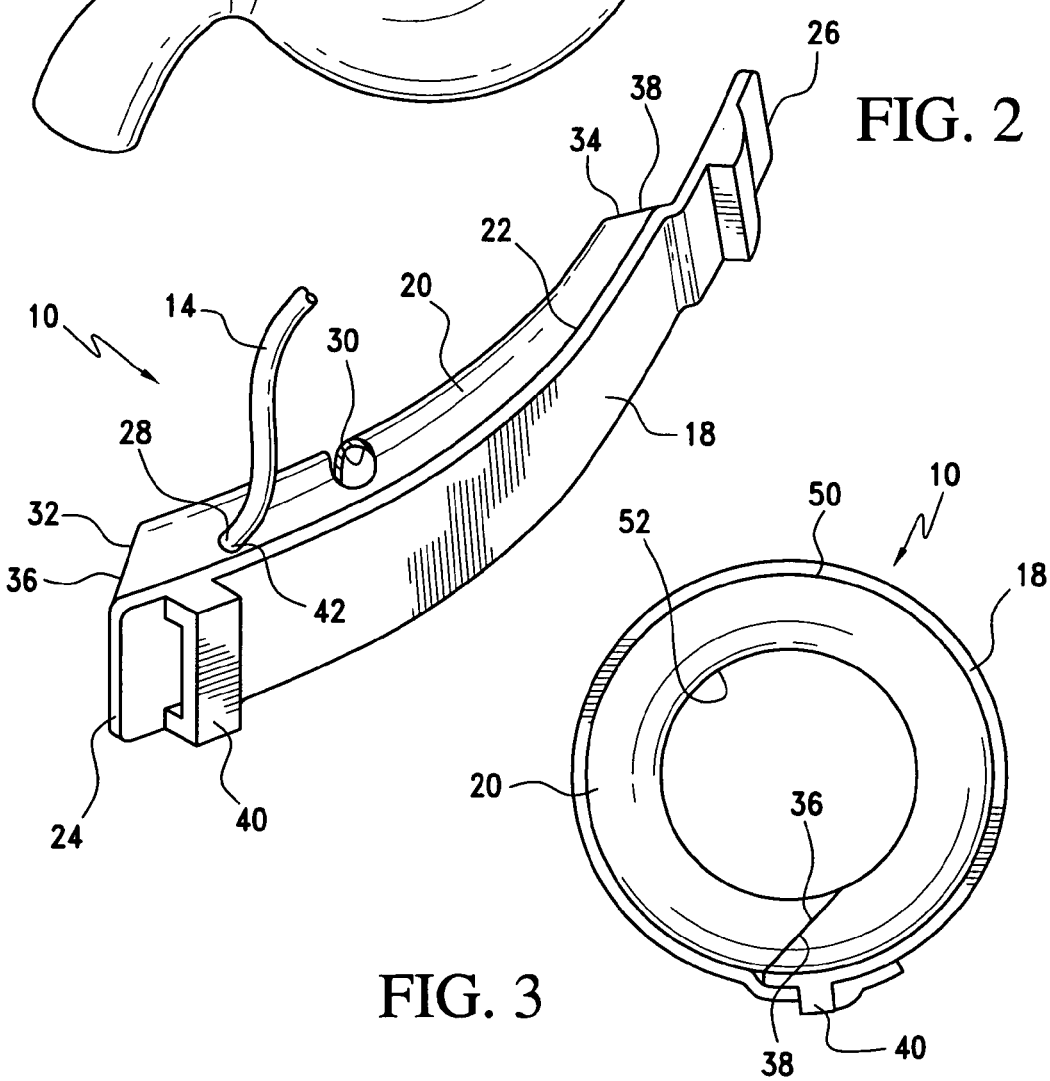
FIG. 2
FIG. 3

GASTRIC BAND WITH MATING END PROFILES

BACKGROUND OF THE INVENTION

1. Field of the Invention

The invention relates to a gastric band. More particularly, the invention relates to a balloon based gastric band having mating ends ensuring a complete loop about the stomach wall.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is a type of gastric reduction surgery attempting to limit food intake by reducing the size of the stomach. In contrast to RYGB and other stomach reduction procedures, gastric banding does not require the alteration of the anatomy of the digestive tract in the duodenum or jejunum.

Since the early 1980s, gastric bands have provided an effective alternative to gastric bypass and other irreversible surgical weight loss treatments for the morbidly obese. Several alternative procedures are performed under the heading of gastric-banding. Some banding techniques employ a gastric ring, others use a band, some use stomach staples and still other procedures use a combination of rings, bands and staples. Among the procedures most commonly performed are lap band, vertical banded gastroplasty (VBG), silastic ring gastroplasty (SRG), and adjustable silastic gastric banding (AGB).

In general, the gastric band is wrapped around an upper portion of the patient's stomach, forming a stoma that is less than the normal interior diameter of the stomach that restricts food passing from an upper portion to a lower digestive portion of the stomach. When the stoma is of an appropriate size, food held in the upper portion of the stomach provides a feeling of fullness that discourages overeating.

Gastric bands with balloon constructions have also been developed. Kuzmak et al., in U.S. Pat. No. 4,592,339, teaches a stoma-adjustable gastric band that includes a balloon section that is expandable and deflatable through a remote injection site. The balloon expandable section adjusts the size of the stoma opening both intraoperatively and post-operatively. During the last several years, manufacturers of prior art bands have improved the designs of the balloons of these bands.

Some balloon based gastric bands create a near 360-degree circumference when closed. When filled and expanded, these balloon based gastric bands provide a near 360-degree pressure interface with the stomach tissue. Although these gastric bands create a near 360-degree circumference, their still remains a gap or pinch point where the first and second ends of the balloon are joined together. As such, a need exists for a gastric band which alleviates this spacing or pinch point so as to ensure a full 360-degree interface with the exterior stomach wall and thereby significantly reduce or eliminate the gap or pinch point found in current balloon based gastric bands. The present invention, therefore, provides such a gastric band.

SUMMARY OF THE INVENTION

It is, therefore, an object of the present invention to provide a gastric band includes a balloon shaped and dimensioned to circumscribe the stomach at a predetermined location. The balloon includes a longitudinally extending body having a first end and second end, the first end and the second end respectively including mating profiles which align to create generally continuous surfaces along an outer surface of the gastric band and an inner surface of the gastric band as the outer surface and the inner surface transition between the first and second ends of the balloon.

It is also an object of the present invention to provide a gastric band wherein the first and second ends are respectively formed with angled surfaces which mate when the first and second ends are brought together It is another object of the present invention to provide a gastric band wherein the first and second ends are respectively formed with tongue and groove profiles which mate when the first and second ends are brought together.

It is a further object of the present invention to provide a gastric band including a fluid supply tube fluidly communicating with the balloon for controlled inflation thereof.

It is also another object of the present invention to provide a gastric band including a fluid injection port in fluid communication with the fluid supply tube.

It is still another object of the present invention to provide a gastric band wherein the balloon is composed of silicone.

It is also an object of the present invention to provide a gastric band including a belt which is composed of silicone.

It is a further object of the present invention to provide a gastric band wherein the balloon is affixed to an inner surface of the belt.

It is yet a further object of the present invention to provide a gastric band including a fastening mechanism for selectively securing the gastric band in an encircled position around a portion of the stomach.

It is also an object of the present invention to provide a gastric band including comprising a belt and a balloon secured to the belt. The balloon and belt are shaped and dimensioned to circumscribe the stomach at a predetermined location. The balloon includes a longitudinally extending body having a first end and second end, the first end and the second end respectively including mating profiles.

It is another object of the present invention to provide a gastric band including a balloon shaped and dimensioned to circumscribe the stomach at a predetermined location. The balloon includes a longitudinally extending body having a first end and second end, which when aligned create generally continuous surfaces along an outer surface of the gastric band and an inner surface of the gastric band as the outer surface and the inner surface transition between the first and second ends of the balloon.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of the present gastric band wrapped about a stomach.

FIG. 2 is a perspective view of the present gastric band.

FIG. 3 is a top view of the present gastric band in its circular configuration.

DESCRIPTION OF THE PREFERRED EMBODIMENT

Figure 4:
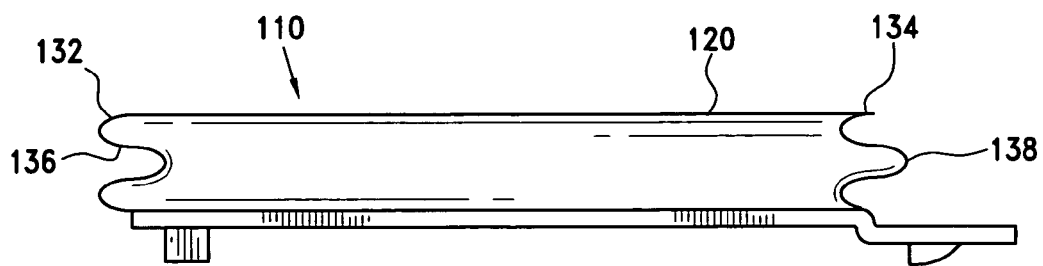
FIGS. 4 and 5 are respectively a side view and top view of an alternate embodiment in accordance with the present invention.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 3, a balloon based gastric band 10 in accordance with the present invention is disclosed. The gastric band 10 is shaped and dimensioned to circumscribe the stomach 12 at a predetermined location reducing the size of the stomach.

A fluid supply tube 14 fluidly communicating with gastric band 10 is in fluid communication with a remotely located fluid injection port 16. The gastric band 10 generally comprises an outer tension carrying belt 18 having an inflatable balloon 20 affixed to the inner surface 22 thereof. When the gastric band 10 is in place, the balloon 20 is inflated, restricting the volume of stomach. To inflate the balloon 20, a filling solution is injected into the injection port 16 and the filling solution is conveyed to the balloon 20 by way of the supply tube 14.

Referring to FIG. 1, the gastric band 10 is shown wrapped around an upper portion of a stomach 12. The gastric band 10 is kept in place by attaching the first and second ends 24, 26 of the band 10 together and extending a portion of the stomach 12 over the gastric band 10 by suturing a portion to the stomach 12.

Referring now to FIGS. 2 and 3, the gastric band 10 in accordance with the present invention is disclosed in greater detail. As briefly mentioned above, the gastric band 10 includes a tension carrying belt 18, a fluid supply tube 14 in fluid communication with a balloon 20 and a remotely located fluid injection port 16. The inflatable balloon 20 is carried along the inner surface 22 of the belt 18. The balloon 20 is secured to the inner surface 22 of the belt 18 in any well known manner, or even made of unitary construction with the belt 18, although the belt 18 is typically formed separately.

A distal end 28 of the fluid supply tube 14 is in fluid communication with the internal cavity 30 of the balloon 20 and the proximal end 27 is in fluid communication with an internal cavity (not shown) of the remote injection port 16.

The balloon 20 is an elongated structure with a first end 32 and a second end 34. The balloon 20 is preferably of a length of about 11 cm. However, those skilled in the art will appreciate the balloon 20 may be of any length which would provide sufficient compression of the stomach 12. The balloon 20 is preferably comprised of material with a thickness between about 0.3 mm and 0.7 mm and more preferably about 0.64 mm. The thickness of the material is dependent on the balloon material and it should be appreciated the thickness of the balloon may vary depending on the balloon composition. In accordance with a preferred embodiment of the present invention, the balloon 20 is manufactured from medical grade silicone, although other known materials, for example, implantable polyurethane, may be used without departing from the spirit of the present invention.

In accordance with a preferred embodiment of the present invention, the balloon 20 is an elongated body with a single cavity. However, various balloon designs could be used within the spirit of the present invention. For example, a multiple segmented balloon as disclosed in U.S. Patent Application Publication No. 2005/0070937, entitled "SEGMENTED GASTRIC BAND", which is incorporated herein by reference, could be employed without departing from the spirit of the present invention.

The balloon 20 is formed with respective mating profiles 36, 38 along the first and second ends 32, 34 thereof. The mating profiles 36, 38 are designed to ensure a full 360-degree interface with the exterior stomach wall and reduce or eliminate the gap or pinch point existing between the first and second ends 32, 34 of the balloon 20 when it is wrapped about the stomach wall and expanded.

Figure 5:
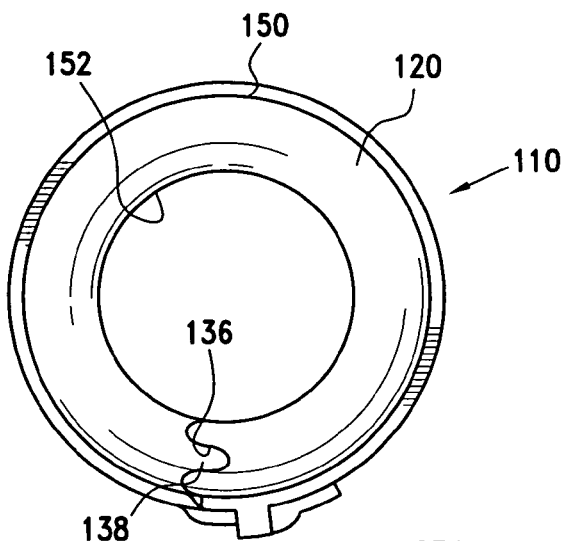
Figure 6:
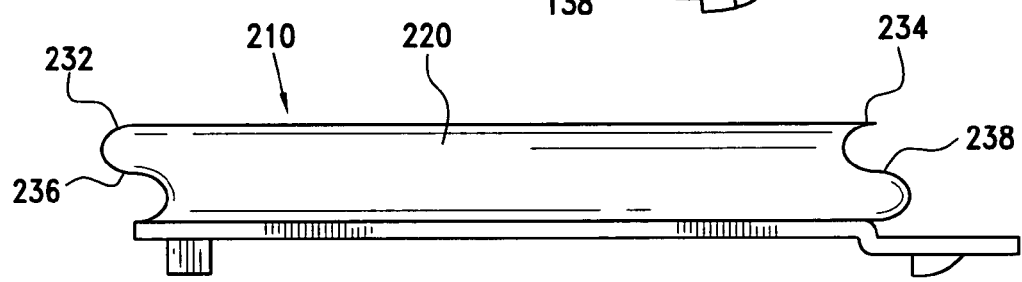
FIGS. 6 and 7 are respectively a side view and top view of another alternate embodiment in accordance with the present invention.
Figure 7:
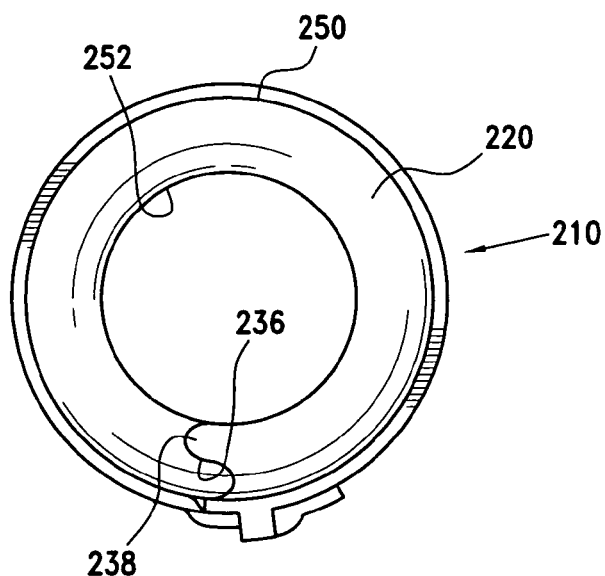

Referring to FIGS. 1, 2 and 3, the first and second ends 32, 34 are respectively formed with angled surfaces 36, 38 which mate as shown in FIG. 3 when the first and second ends 32, 34 are brought together forming the balloon 20 in a loop about the exterior stomach wall. FIGS. 4 through 7 show the first and second ends 132, 232, 134, 234 are respectively formed with tongue and groove profiles 136, 236, 138, 238 which mate as shown in FIG. 5 and 7 when the first and second ends 132, 232, 134, 234 are brought together forming the balloon 120, 220 in a loop about the exterior stomach wall. As those skilled in the art will appreciate, a wide variety of possible designs relating to the end profiles that may be employed in accordance with the present invention are possible within the spirit of the present invention.

As mentioned above, the ends of the balloon 20, 120, 220 are formed to create a mating relationship between the first and second ends 32, 132, 232, 34, 134, 234 thereof. This mating relationship creates generally continuous surfaces along the outer surface 50, 150, 250 of the gastric band 10, 110, 210 and the inner surface 52, 152, 252 of the gastric band 10, 110, 210. By providing the first and second ends 32, 132, 232, 34, 134, 234 of the balloon 20, 120, 220 with mating profiles, the outer and inner surfaces 50, 150, 250, 52, 152, 252 of the gastric band 10, 110, 210 are substantially continuous as they transition between the first and second ends 32, 132, 232, 34, 134, 234 of the balloon 20, 120, 220 and form a continuous ring.

The tension carrying belt 18 is slightly longer than the balloon 20 and may be of any suitable length sufficient to accommodate the type of latching mechanism 40 employed. As with the balloon 20 itself, the carrying belt 18 is composed of medical grade silicone polymer but may be composed of any flexible biocompatible material, for example, implantable polyurethane, without departing from the spirit of the present invention.

The gastric band 10, and more particularly, the tension carrying belt 18, is provided with a latching mechanism 40 so that the gastric band 10 may be releasably secured in an encircled position around a portion of the stomach 12. Various latching mechanism may be used within the spirit of the present invention. Some of these latching mechanisms are disclosed in U.S. Published Patent Application Ser. Nos. 2005/0002984, entitled "IMPLANTABLE BAND WITH ATTACHMENT MECHANISM HAVING DISSIMILAR MATERIAL PROPERTIES", 2004/0267291, entitled "IMPLANTABLE BAND WITH NON-MECHANICAL ATTACHMENT MECHANISM", 2004/0267292, entitled "IMPLANTABLE BAND WITH TRANSVERSE ATTACHMENT MECHANISM", 2004/0267288, entitled "IMPLANTABLE BAND HAVING IMPROVED ATTACHMENT MECHANISM", and 2004/0267293, entitled "IMPLANTABLE BAND WITH ATTACHMENT MECHANISM", which are incorporated herein by reference.

As mentioned above, the balloon 20 is provided with a fluid supply tube 14 coupled to a remote injection port 16. The fluid supply tube 14 includes inlets 42 providing access to the internal cavity 30 of the balloon 20. The remote injection port 16 includes a silicone septum. At the time the adjustable gastric band 10 is implanted around a portion of the stomach 12, the remote injection port 16 is also implanted at a suitable location, usually within the rectus sheaths, for transcutaneous access via a Huber needle. Examples of injection port structures which may employed in accordance with the present invention are disclosed in U.S. Patent Application Publication Ser. Nos. 2004/0254536, entitled "SUBCUTANEOUS SELF ATTACHING INJECTION PORT WITH INTEGRAL FASTENERS", and 2004/0254537, entitled "SUBCUTANEOUS SELF ATTACHING INJECTION PORT WITH INTEGRAL MOVEABLE RETENTION MEMBERS", which are incorporated by reference.

The internal cavity 30 of the balloon 20 is evacuated prior to installation. The fluid supply tube 14 and the internal cavity of the remote injection port 16 are preferably supplied with physiologically compatible fluids, such as a saline or radiopaque solutions, during postoperative adjustment. Postoperative adjustment of the perimeter enclosed by the balloon 20, and therefore the size of the stoma, is accomplished by the addition or removal of fluid from the internal cavity 30 of the balloon 20 by inserting a Huber needle percutaneously into the silicone septum of the injection port 16.

Installation of the gastric band 10 is accomplished by first inserting the band 10 into the patient's abdomen through a trocar. Next, a tunnel is created behind the stomach 12 near the esophagogastric junction using a blunt dissection device. The gastric band 10 is then grasped by an instrument, such as a grasper or blunt dissection device, and wrapped around the patient's stomach 12 through the created tunnel. The latching mechanism 40 is then engaged. The injection port 16 is then attached to the gastric band 10 and the injection port 16 is secured subcutaneously in the abdomen or other suitable location. A suitable filling solution, such as saline, is then injected into injection port 16 whereby the solution is conveyed to the internal cavity 30 of the balloon by way of inlets 42 in fluid supply tube 14. If necessary either at the time the gastric band 10 is installed or at some time in the future, a predetermined quantity of the filling solution may be withdrawn for the balloon 20 by inserting a syringe into the injection port 16 and withdrawing the solution.

Although the present invention is described for use in conjunction with gastric bands, those skilled in the art will appreciate the above invention has equally applicability to other types of implantable bands. For example, bands are used for the treatment of fecal incontinence. One such band is described in U.S. Pat. No. 6,461,292. Bands can also be used to treat urinary incontinence. One such band is described in U.S. Patent Application Publication Ser. No. 2003/0105385. Bands can also be used to treat heartburn and/or acid reflux. One such band is described in U.S. Pat. No. 6,470,892. Bands can also be used to treat impotence. One such band is described in U.S. Patent Application Publication Ser. No. 2003/0114729.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A gastric band, comprising:
a balloon shaped and dimensioned to circumscribe the stomach at a predetermined location;
the balloon includes a longitudinally extending body having a first end and second end, the first end and the second end respectively including mating profiles which align to create a generally continuous surface along an inner surface of the gastric band as the inner surface transitions between the first and second ends of the balloon; and
wherein the first and second ends are respectively formed with tongue and groove profiles which mate when the first and second ends are brought together.

2. The gastric band according to claim 1, further including a fluid supply tube fluidly communicating with the balloon for controlled inflation thereof.

3. The gastric band according to claim 2, further including a fluid injection port in fluid communication with the fluid supply tube.

4. The gastric band according to claim 1, wherein the balloon is composed of silicone.

5. The gastric band according to claim 4, further including a belt, and wherein the balloon is affixed to an inner surface of the belt.

6. The gastric band according to claim 5, wherein the balloon and belt are composed of silicone.

7. The gastric band according to claim 1, further including a fastening mechanism for selectively securing the gastric band in an encircled position around a portion of the stomach.

8. A gastric band, comprising:
a belt including a first end and a second end, the first end of the belt and the second end of the belt including respective mating fastening members for selectively securing the gastric band in an encircled position around a portion of the stomach;
a balloon secured to the belt, the balloon and belt being shaped and dimensioned to circumscribe the stomach at a predetermined location;
the balloon includes a longitudinally extending body having a first end and second end, the first end of the balloon and the second end of the balloon respectively including mating profiles which align to create a generally continuous surface along an inner surface of the gastric band as the inner surface transitions between the first and second ends of the balloon;
wherein the first and second ends of the balloon are respectively formed with angled surfaces which mate when the first and second ends of the balloon are brought together.

9. A gastric band, comprising:
a belt including a first end and a second end, the first end of the belt and the second end of the belt including respective mating fastening members for selectively securing the gastric band in an encircled position around a portion of the stomach;

a balloon shaped and dimensioned to circumscribe the stomach at a predetermined location;

the balloon includes a longitudinally extending body having a first end and second end, the first end of the balloon and the second end of the balloon respectively including mating profiles which align to create a generally continuous surface along an inner surface of the gastric band as the inner surface transitions between the first and second ends of the balloon; and wherein the first and second ends of the balloon are respectively formed with angled surfaces which mate when the first and second ends of the balloon are brought together.

* * * * *